United States Patent
Sambanthamurthi et al.

(10) Patent No.: US 11,033,596 B2
(45) Date of Patent: Jun. 15, 2021

(54) ANTIOXIDANT, ANTI-INFLAMMATORY COMPOSITIONS AND USES THEREOF

(71) Applicant: Malaysian Palm Oil Board, Selangor (MY)

(72) Inventors: Ravigadevi Sambanthamurthi, Kajang (MY); Tan Yew AI, Kajang (MY); T. G. Sambandan, Cambridge, MA (US); Cho Kyun Rha, Cambridge, MA (US); Anthony J. Sinskey, Cambridge, MA (US)

(73) Assignee: MALAYSIAN PALM OIL BOARD, Kajang (MY)

( * ) Notice: Subject to any disclaimer, the term of this patent is extended or adjusted under 35 U.S.C. 154(b) by 733 days.

(21) Appl. No.: 15/462,433

(22) Filed: Mar. 17, 2017

(65) Prior Publication Data
US 2018/0264066 A1 Sep. 20, 2018

(51) Int. Cl.
*A61K 36/889* (2006.01)
*A61K 31/191* (2006.01)
*A61K 31/192* (2006.01)
*A61K 31/235* (2006.01)

(52) U.S. Cl.
CPC .......... *A61K 36/889* (2013.01); *A61K 31/191* (2013.01); *A61K 31/192* (2013.01); *A61K 31/235* (2013.01)

(58) Field of Classification Search
CPC .. A61K 31/191; A61K 31/192; A61K 31/235; A61K 36/889
See application file for complete search history.

(56) References Cited

U.S. PATENT DOCUMENTS 9,610,313 B2 * 4/2017 Minatelli .............. A23L 33/105

FOREIGN PATENT DOCUMENTS

WO WO-2012067491 A2 * 5/2012 ........... A61K 31/192

\* cited by examiner

*Primary Examiner* — Aaron J Kosar
(74) *Attorney, Agent, or Firm* — Maschoff Brennan

(57) ABSTRACT

Compositions comprising oil palm phenolics and shikimic acid or derivatives thereof and their use in enhancing anti-oxidative and anti-inflammatory properties.

6 Claims, 1 Drawing Sheet

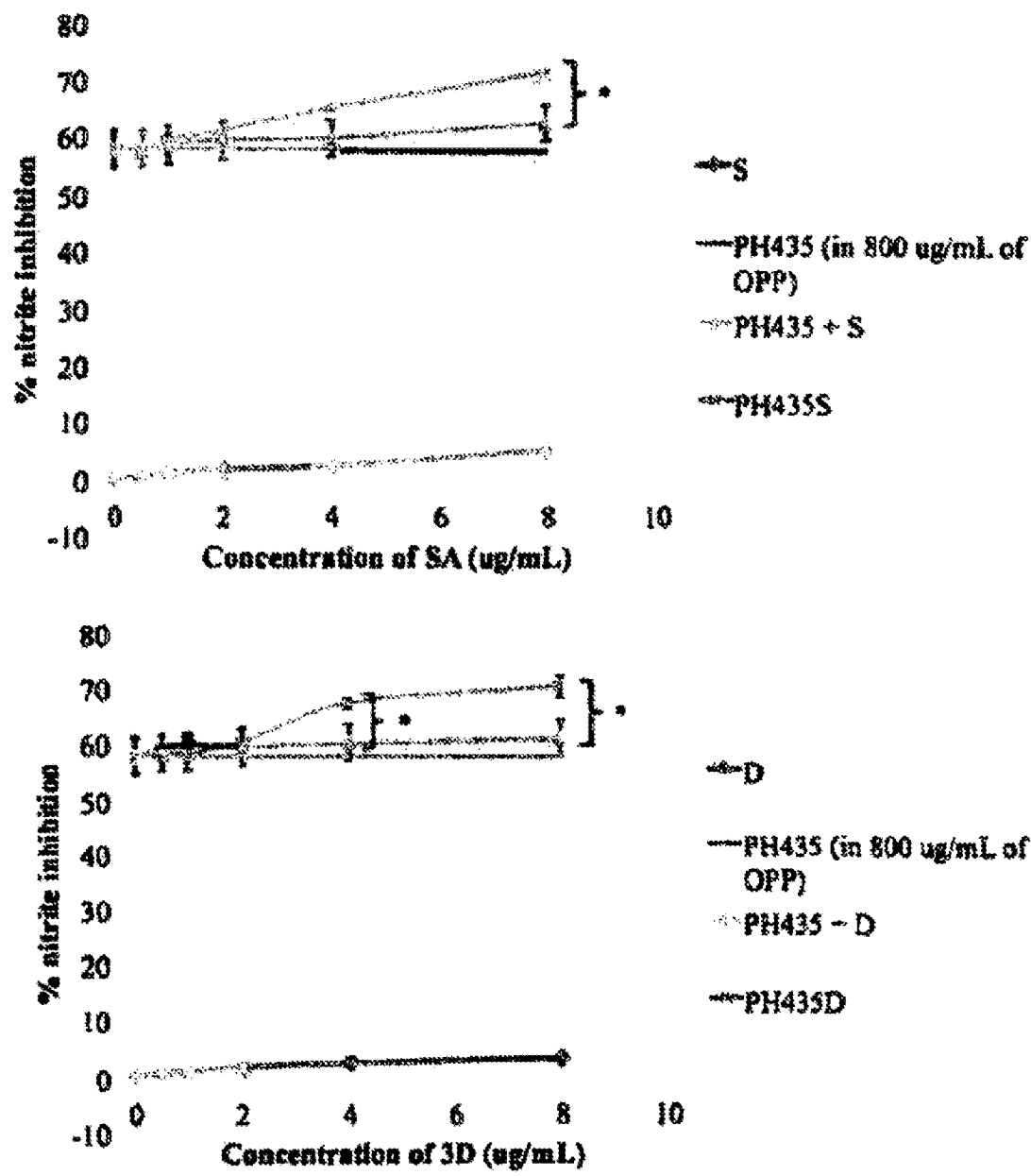

ANTIOXIDANT, ANTI-INFLAMMATORY COMPOSITIONS AND USES THEREOF

FIELD OF INVENTION

The present invention relates to compounds having synergistic antioxidant and anti-inflammatory properties. More particularly, the present invention relates to compounds enhancing properties of anti-oxidative and anti-inflammatory agents.

BACKGROUND OF THE INVENTION

The normal functioning of life requires, inter alia, proper balance between formation and elimination of damaging substances. Oxidative stress, for example, represents an imbalance between the levels of damaging oxidizing species, such as reactive oxygen species (ROS) and reactive nitrogen species (RNS). The insufficient ability of a biological system to readily neutralize or eliminate the oxidizing species leads to deleterious modifications of cellular proteins, lipids and DNA.

Oxidative stress and inflammation are implicated in the pathogenesis of metabolic diseases, diabetes, obesity, dyslipidemia and their associated cardiovascular complications. Oxidative stress is also associated with a wide range of diseases and other medical conditions such as Alzheimer's disease, Parkinson's disease, rheumatoid arthritis, neurodegeneration, airway inflammation and hyper-responsiveness (e.g. asthma), and some skin disorders, such as vitiligo. In addition to pathological conditions, oxidative stress is also known to be involved in some undesired components of aging.

As to inflammation, clinical studies suggest that acute hyperglycemia results in elevated levels of circulating inflammatory cytokines such as TNFa, IL6, and IL18. During hyperglycemia and/or hyperlipidemia, mitochondria generate cellular energy through TCA cycle activity and the associated electron transport chain of the inner mitochondrial membrane. However, while mitochondria generate elevated ATP production, mitochondria can also generate significant reactive oxygen species (ROS) and reactive nitrogen species (RNS).

The cells are equipped with several antioxidant enzymes to neutralize ROS and RNS. However, while cells have a number of available anti-oxidant mechanisms, damage most likely occurs when the ROS is excessive and/or anti-oxidant pathways are overwhelmed.

In many cases, lowering the oxidative stress leads to improvement in the disease manifestation. In many other cases, lowering the oxidative stress may prevent the disease outbreak.

In our own earlier work, we have shown that phenolic anti-oxidants vis caffeoylshikimic acid, p-hydroxybenzoic acid in compositions, such as Oil Palm Phenolics (OPP), are responsible for the anti-oxidative and anti-inflammatory activity. For e.g. phenolic compounds have been shown to be strong antioxidants, comparable with many known reducing molecules in several assays (Bala Balasundram et al (2005): "Antioxidant properties of palm fruit extracts", *Asia Pacific Journal of Clinical Nutrition*, 14(4), 319-324). Gene expression studies have also shown the anti-oxidative and anti-inflammatory effects of Oil Palm Phenolics in mammalian cells (Sambanthamurthi R. et al. (2013): "OPP attenuate changes caused by an atherogenic diet in mice". *European Journal of Nutrition*, 52(2), 443-456).

However, there still remains a need in the art for enhancing the treatment of metabolic disorders by way of ameliorating the inflammatory and oxidative processes associated with such disorders.

SUMMARY OF THE INVENTION

Various embodiments of the present invention provide a composition comprising oil palm phenolics and shikimic acid or derivatives thereof.

The present invention further provides use of shikimic acid or derivatives thereof to enhance anti-oxidative properties of anti-oxidative agents.

The present invention further provides a method of ameliorating oxidative stress or inflammation comprising: administering to a subject a therapeutically effective amount of a composition comprising oil palm phenolics and shikimic acid or derivatives thereof.

The present invention further provides use of a composition comprising shikimic acid and 3-dehydroshikimic acid in ameliorating oxidative stress, inflammation or related disorders.

Other objects, features, and advantages of the invention will be apparent from the following description when read with reference to the accompanying drawings.

BRIEF DESCRIPTION OF THE DRAWINGS

FIG. 1 is a graphical representation of the biological enhancement of chemical combination of major compounds of Oil Palm phenolics in cell-based $NO_2^-$ scavenging activity (Griess assay, RAW macrophages, Mean±SE).

DETAILED DESCRIPTION

The present invention will now be described in detail with reference to the accompanying in drawings.

Various embodiments of the present invention provide a composition comprising oil palm phenolics and shikimic acid or derivatives thereof.

According to an embodiment of the invention, shikimic acid derivatives include 3-dehydroshikimic acid.

According to another embodiment of the present invention, oil palm phenolics are selected from protocatechuic acid, p-hydroxybenzoic acid, 4-caffeoylshikimic acid, 3-eaffecylshikimic acid, 5-caffeoylshikimic acid or mixtures thereof.

According to yet another embodiment of the present invention, the composition optionally comprises bioactive compounds selected from the group consisting of peptides, minerals, oligosaccharides and mixtures thereof.

According to an embodiment of the present invention, the composition further comprises pharmaceutically acceptable carriers.

According to an embodiment, the composition optionally comprises one or more diluents. Non-limiting examples of diluents include dextrose, maltodextrin, saline, buffered saline, water, glycerol and ethanol.

The composition of the present invention comprising oil palm phenolics may also comprise more than one component of other anti-oxidative stress and/or anti-inflammatory agents such as drugs, quasi-drugs, foods or beverages used for this purpose.

The composition of the present invention may be formulated in any form. The formulation can be prepared as injectable preparation (true solution, suspension, or emulsion), oral dosage form (tablet, capsule, soft capsule, aqueous medicine, pill, granule,) topical preparation (ointment, patch, spray, solution, and the like.

According to an embodiment, the composition is applied topically, as a skin dermal patch, as a skin spray or as a nasal or intravenous solution.

According to an embodiment, the present invention relates to use of shikimic acid or derivatives thereof to enhance anti-oxidative properties of anti-oxidative agents.

According to another embodiment of the present invention, the anti-oxidative agents are oil palm phenolics selected from the group comprising of protocatechuic acid, p-hydroxybenzoic acid, 4-caffeoylshikimic acid, 3-eaffecyl-shikimic acid, 5-caffeoylshikimic acid and mixtures thereof.

According to yet another embodiment, the present invention relates to use of shikimic acid or derivatives thereof to enhance anti-inflammatory properties of anti-inflammatory agents.

According to another embodiment of the present invention, the anti-inflammatory agents are oil palm phenolics selected from the group comprising of protocatechuic acid, p-hydroxybenzoic acid, 4-caffeoylshikimic acid, 3-eaffecyl-shikimic acid, 5-caffeoylshikimic acid and mixtures thereof.

According to still another embodiment, the present invention provides a method of ameliorating oxidative stress or inflammation comprising: administering to a subject a therapeutically effective amount of the composition as claimed in claim 1.

According to an embodiment of the present invention, the composition inhibits nitrite in biological systems.

According to an embodiment of the present invention, the composition inhibits ROS (Reactive Oxygen Species) in biological systems.

According to an embodiment of the present invention, the composition is applied topically, as a skin dermal patch, as a skin spray or as a nasal or intravenous solution.

According to an embodiment, the present invention further relates to use of a composition comprising shikimic acid and 3-dehydroshikimic acid in ameliorating oxidative stress, inflammation or related disorders.

The following examples are provided to illustrate certain particular features and/or embodiments. These examples should not be construed to limit the disclosure to the particular features or embodiments disclosed therein

EXAMPLES

For the sake of convenience, the following abbreviations will be used in the following examples:
Abbreviations
Protocatechuic acid (P);
p-hydoxybenzoic acid (H);
3-dehydroshikiinic acid (D);
caffeoylshikimic acid (C);
4-caffeoylshikimic acid (4);
3-caffeoylshikimic acid (3);
5-caffeoylshikimic acid (5);
Shikimic acid (S)
Chemical combination of PH435 and S (PH435S);
Chemical combination of PH435 and D (PH435D);
Mathematical sum of % inhibition of $NO_2^-$(PH435+S);
Mathematical sum of % inhibition of $NO_2^-$(PH435+D)

Example 1

Nitrite Measurement (Sodium Nitroprusside—SNP Assay)

SNP in aqueous solution at physiological pH spontaneously generates nitric oxide, which interacts with oxygen to produce a nitrite ion that can be estimated by using griess reagent.

In this assay, shikimic acid and 3-dehydroshikimic acid exhibit a low inhibition of the nitrite ion However, it does not show any enhancement when added along with p-hydroxybenzoic acid, the compound that is present in large quantity in OPP. 3-dehydroshikimic acid, exhibited a similar effect as shikimic acid in this chemical system. This result may be because the assay measures only the chemical activity.

The 4 combinations of OPP, PH435, PH435S, PH435D were found to exhibit very similar percentages of nitrite inhibition, without any enhancement by shikimic acid and 3-dehydroshikimic acid.

Cell-Based Systems:

Example 2

$H_2O_2$ Measurement (Cell-Based Antioxidant Protection in Erythrocytes CAP-e Assay)

Red blood cells can be used as a cellular model to quantify reactive oxygen species (ROS). As these cells lose their nuclei at the erythroblast stage, they cannot perform transcription and translation for bringing about genetic and protein level changes. Hence, the ROS measurement signifies the ability of the antioxidant compound to enter the cytosol and quench free radicals.

In this method, shikimic acid does not show any effect on reducing ROS. However, all the other compounds are able to inhibit H2O2 oxidation. Both HCS and HCD combinations are synergistic as they are greater than H+C+S and H+C+D respectively. An interesting observation is that the chemical combination of HCS, the predominant compounds of OPP, is able to explain only 78% of the inhibition of ROS by ON). However, when 3-dehydroshikimic acid is added along with H and C, it leads to 93% inhibition of ROS when compared to OPP. The results are shown in Table 1 below:

TABLE 1

| Cell-based ROS scavenging activity (CAP-e assay) | | | |
|---|---|---|---|
| Description | Amount added (mM) # | Actual % inhibition of ROS | % inhibition of ROS in comparison to Oil Palm phenolics(±S.E.) |
| p-hydoxybenzoic acid (H) | 0.51 | 22.5 | 30.6 (±0.2) |
| Caffeoylshikimic acid (C) | 0.3 | 25.9 | 35.2(±0.1) |
| Shikimic acid (S) | 0.57 | -Not detected- | -Not detected- |
| 3dehydrosbikimic acid (D) | 0.58 | 9.9 | 13.4 (±0.05) |
| Mathematical sum (H + C + S) of % inhibition of ROS | | 48.4 | 65.7(±0.2) |
| Mathematical sum (H + C + D) of % inhibition of | | 58.3 | 79.2 (±0.2) |

TABLE 1-continued

Cell-based ROS scavenging activity (CAP-e assay)

| Description | Amount added (mM) # | Actual % inhibition of ROS | % inhibition of ROS in comparison to Oil Palm phenolics(±S.E.) |
|---|---|---|---|
| ROS Chemical combination (HCS) by adding the 3 components at above-mentioned amounts together | 57.4 | | 77.9 (±0.6) |
| Chemical combination (HCD) by adding the 3 components at above-mentioned amounts together | 68.5 | | 93 (±0.8) |
| Oil Palm Phenolics | 10 mg/mL | 73.7 | 100 (±0.8) |

Components were added according to the concentration present in 10 mg/mL of OPP.
*All values show statistical significance in comparison to OPP (P < 0.01, Tukey-Kramer Honestly Significant Differences test)

Example 3

$H_2O_2$ Measurement (Cell-Based Antioxidant Protection in Granulocytesipolymorphonuclear—PMN Cells Assay)

Shikimic acid shows inhibitory action in the two assays that measure the anti-inflammatory and anti-oxidative activity: 1) Cell-based griess assay 2) Cell-based PMN assay and the nitrite scavenging assay: 3) Chemical-based SNP assay. However, it is able to enhance the anti-inflammatory and anti-oxidative activity of other components only in the two cell-based assays (Griess and PMN). In RBC cells, it shows no activity as it lacks direct antioxidant activity.

3-dehydroshikirnic acid shows inhibitory action in the three assays that measure the anti-inflammatory and anti-oxidative activity: 1) Cell-based griess assay 2) Cell-based PMN assay 3) Cell-based CAP-e assay and the nitrite scavenging assay: 4) Chemical-based SNP assay. However, its enhancement effect could be seen in 1) cell-based griess assay 2) Cell-based PMN assay 3) Cell-based CAP-e assay and 4) the chemical-based ORAC assay.

FIG. 1 and Table 2 show the synergistic effect of the composition in cell based nitrite scavenging activity.

For the study, PH435 composition was prepared according to the concentration present in 800 μg/mL of Oil Palm Phenolics. From FIG. 1 and Table 5 (below), it can be seen that the nitrite scavenging activity of the combinations of Protocatechuic acid, p-hydoxybenzoic acid, 4-caffeoylshikimic acid, 3-caffeoylshikimic acid with 3-dehydroshikiinic acid and Shikimic acid is significantly higher than the composition of Oil palm phenolics.

TABLE 2

| Description | Amount added(μM) ‡ | Actual % inhibition of ROS | % inhibition of ROS in comparison to Oil Palm phenolics (± S.E) |
|---|---|---|---|
| Protocatechuic acid (P) | 3.3 | 8.6 | 13 (±0.7) |
| p-hydoxybenzoic acid (H) | 40.5 | 11.4 | 17.3(±2.8) |
| 4-Caffeoylshikimic acid (4) | 7.1 | 8.4 | 12.7(±2.5) |
| 3-Caffeoylshikimic acid (4) | 8.1 | 12.3 | 18.6(±2.3) |
| 5-Caffeoylshikimic acid (4) | 10.2 | 8.8 | 13.4(±3.7) |
| Shikimic acid (S) | 45.9 | 3.4 | 5.2 (±0.7) |
| Mathematical sum (P + H + 4 + 3 + 5) of % inhibition of $NO_2^-$ | 49.4 | | 75(±5.8) |
| Mathematical sum (P + H + 4 + 3 + 5 + S) of % inhibition of $NO_2^-$ | 52.9 | | 80.2 (±5.8) |
| Chemical combination (PH435) by adding the 5 components at above-mentioned amounts together | 56.3 | | 85.4 (±1.7) |
| Chemical combination (PH435S) by adding the 6 components at above-mentioned amounts together | 62 | | 94.1 (±0.8)* |
| Oil Palm Phenolics | 800 μg/mL | 65.9 | 100 (±3.2) |

‡ Components were added according to the concentration present in 800 μg/mL of OPP
*All components except PH435S show statistical significance (p < 0.05) with respect to OPP using Tukey-Kramer's Honestly Significant Difference (HSD)

It can be deduced that the presence of AMP (nucleotide Adenosine Monophosphate) as part of its structure may be required by shikimic acid in order to exhibit its enhancement effect. Attaining such a structure is only possible in a cell-based system. It may also be possible that shikimic acid cannot get converted into its active form 3-dehydroshikimic acid in RBC cells due to lack of GDH, but the conversion can be possible in granulocytes. It could also be a result of the anti-inflammatory and anti-oxidative signaling actions by shikimic acid in combination with other components.

It is to be understood that various modifications and changes may be made or various alternative standard/conventional procedures may be employed without departing from the spirit and scope of the present invention and the same should be construed to be within the scope of the present invention.

We claim:

1. A composition for inhibiting reactive oxygen species (ROS) in a cell-based system consisting of:
   a therapeutically effective amount of oil palm phenolics and shikimic acid or derivatives obtained from palm oil vegetation liquor, wherein the oil palm phenolics and shikimic acid or derivatives are comprised of a combination of p-hydroxybenzoic acid, caffeoylshikimic acid, and 3-dehydroshikimic acid; and
   at least one pharmaceutically acceptable carrier or at least on diluent selected from the group consisting of dextrose, maltodextrin, saline, buffered saline, water, glycerol, and ethanol.

2. The composition of claim 1, wherein shikimic acid derivatives include 3-dehydroshikimic acid.

3. The composition of claim 1, wherein oil palm phenolics are selected from the group consisting of protocatechuic acid, p-hydroxybenzoic acid, 4-caffeoylshikimic acid, 3-eaffecylshikimic acid, and 5-caffeoylshikimic acid and mixtures thereof.

4. The composition of claim 1, further comprising bioactive compounds selected from the group consisting of peptides, minerals, and oligosaccharides and mixtures thereof.

5. The composition of claim 1, further comprising pharmaceutically acceptable carriers.

6. The composition of claim 1, wherein the composition is applied topically, as a skin dermal patch, as a skin spray or as a nasal or intravenous solution.

\* \* \* \* \*